Figure 1:
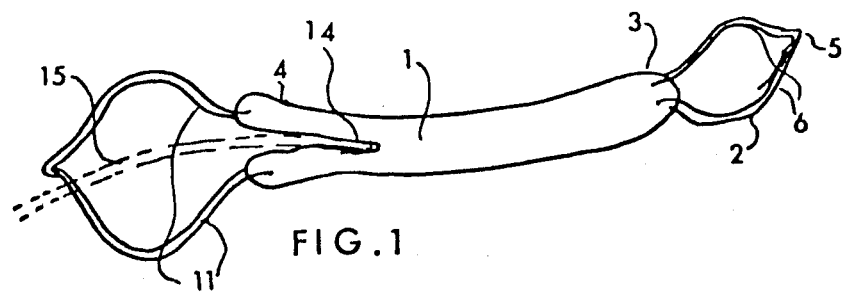

United States Patent [19]

Hamou

[11] Patent Number: 4,595,000
[45] Date of Patent: Jun. 17, 1986

[54] TUBULAR PESSARY AS A CONTRACEPTIVE MEANS

[76] Inventor: Jacques Hamou, 2 - Chaussee De LaMuette, 75016 Paris, France

[21] Appl. No.: 612,758

[22] Filed: May 21, 1984

Related U.S. Application Data

[63] Continuation-in-part of Ser. No. 553,466, Nov. 18, 1983.

[30] Foreign Application Priority Data

Mar. 23, 1983 [WO] PCT Int'l Appl. ... PCT/DE83/00047

[51] Int. Cl.⁴ ............................................. A61F 5/46
[52] U.S. Cl. .................................................. 128/130
[58] Field of Search ............... 128/129, 127, 128, 130

[56] References Cited

U.S. PATENT DOCUMENTS

| | | | |
|---|---|---|---|
| 3,757,775 | 9/1973 | Marco et al. | 128/130 |
| 3,840,005 | 10/1974 | Walker | 128/130 |
| 3,842,826 | 10/1974 | Nolan | 128/130 |
| 3,937,217 | 2/1976 | Kosonen | 128/130 |
| 4,198,966 | 4/1980 | Kaivola | 128/130 |

Primary Examiner—John D. Yasko
Attorney, Agent, or Firm—Donald D. Mon

[57] ABSTRACT

Tubular pessary as a contraceptive means, which can be carried or worn on either side by hysteroscopy.

The invention relates to a tubular pessary having a contraceptive action through the obturation of the proximal uterine tube in non-surgical manner by hysteroscopy and which can easily be worn on either side.

The tubular pessary has a cylindrical, sensitive central part permitting the obturation of the uterine tube. It has a distal elastic loop, which prevents sliding back into the uterus of the device. It has a proximal elastic loop, which prevents migration of the device into the abdominal cavity and which can easily be removed through a hysteroscope.

The object of the invention is to overcome the inadequacies of the known contraceptive means.

6 Claims, 7 Drawing Figures

TUBULAR PESSARY AS A CONTRACEPTIVE MEANS

The invention relates to a tubular pessary as a contraceptive means by non-surgical hysteroscopy and which women can carry or wear on either side.

All the known methods and devices of this type have limits, with regards to application and effectiveness.

Ideally, a contraceptive means must have a 100% efficiency, but enable unimpeded sexual intercourse, being comfortable to wear, inexpensive and in particular having a reversible action.

Already, numerous contraceptive means are known, e.g. devices which are inserted into the vagina, condoms and the like, but these are not completely effective. Devices which are inserted into the uterus, such as IUD's have the disadvantage of causing bleeding and pain, as a result of contact in the uterus with the discharges thereof. This makes regular replacement necessary in order to physically modify the surfaces and also adapt to chemical menstruation. Contraceptive pills on a hormone base lead to the known side-effects. Sterilization by ligation of the uterine tube, resection, rings or clamps, leading to irregularity in the funnel-shaped ectasias, are also disadvantageous. Thus, these methods require surgery and it is difficult, if not impossible, to restore receptivity for normal reproduction.

Finally, means exist for closing the trumpet-shaped ectasias by injection using a hysteroscope, using a mixture of a liquid pre-elastomer and a catalyst injected for polymerizing the material in the uterine tube. However, this requires a special technique with a local anesthetic, requiring a pumping device for injection. There is also a possibility of failure and the increased risks, due more particularly to the instability of the injection material. Reversibility through the use of hysteroscopy is theoretically possible, but the passage of the distal outer end of the syringe having a diameter of several millimetres can injure the isthmian canal of the trumpet-shaped ectasia with a diameter below 1 mm, despite the elasticity of the elastomer.

The problem of the invention is to overcome the aforementioned disadvantages of known contraceptive means and to provide a novel, non-surgical technique, which is easy to use, inexpensive and reversible.

The aim is to provide a tubular pessary, which permits an obturation by using a hysteroscope, as is generally known in the field of gynecology, through which the device can be very easily removed, or in which a clamp is used.

The invention is described in greater detail hereinafter relative to non-limitative embodiments and the attached drawings, wherein shown:

FIG. 1 a diagrammatic first embodiment of the tubular pessary.

Figure 2:
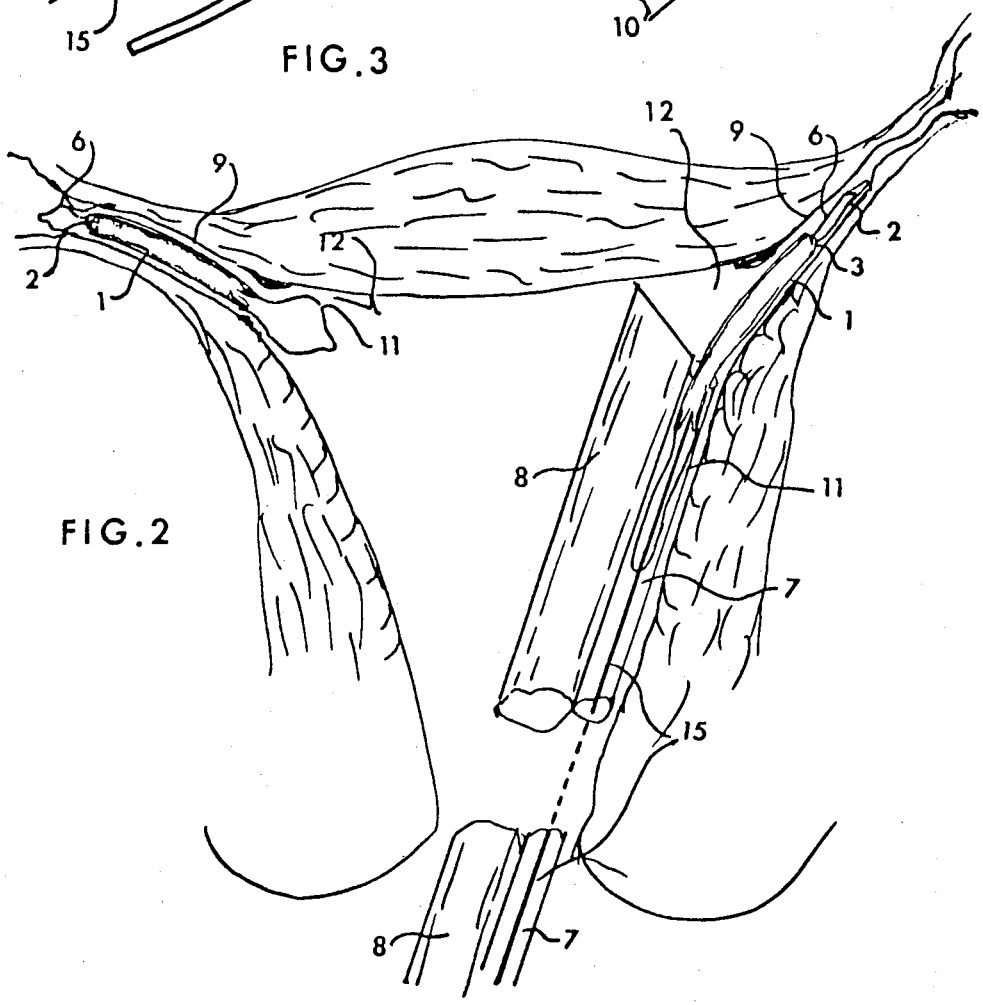

FIG. 2 the tubular pessary of FIG. 1 in its operative position.

Figure 3:
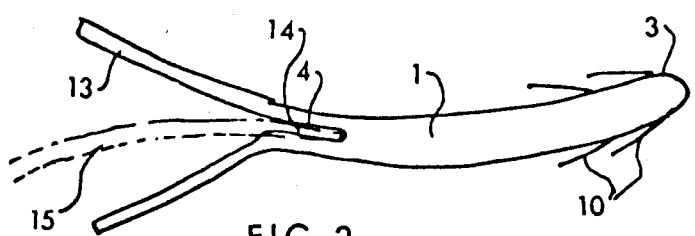

FIG. 3 another embodiment of the tubular pessary.

Figure 4:
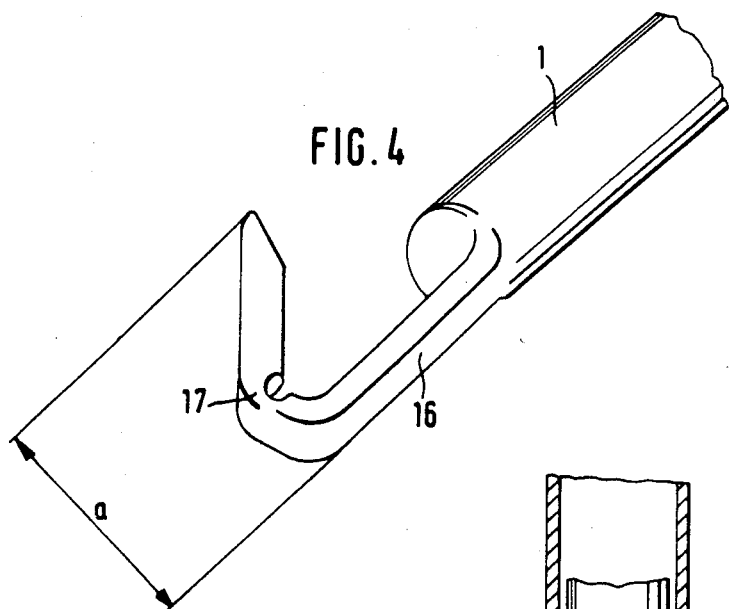

FIG. 4 a view of only the distal end of a further extending embodiment.

Figure 5:
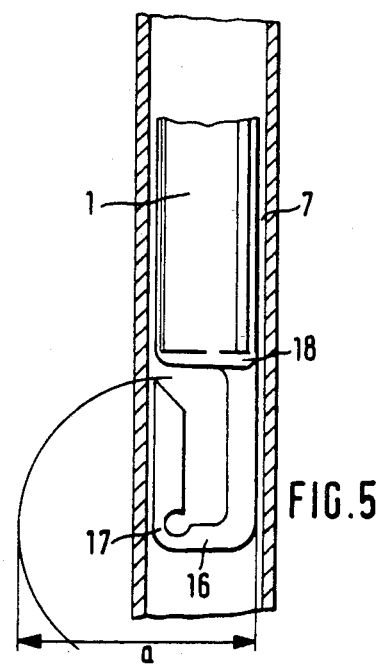

FIG. 5 a partial section through the channel with the distal end of the device according to FIG. 4.

Figure 6:
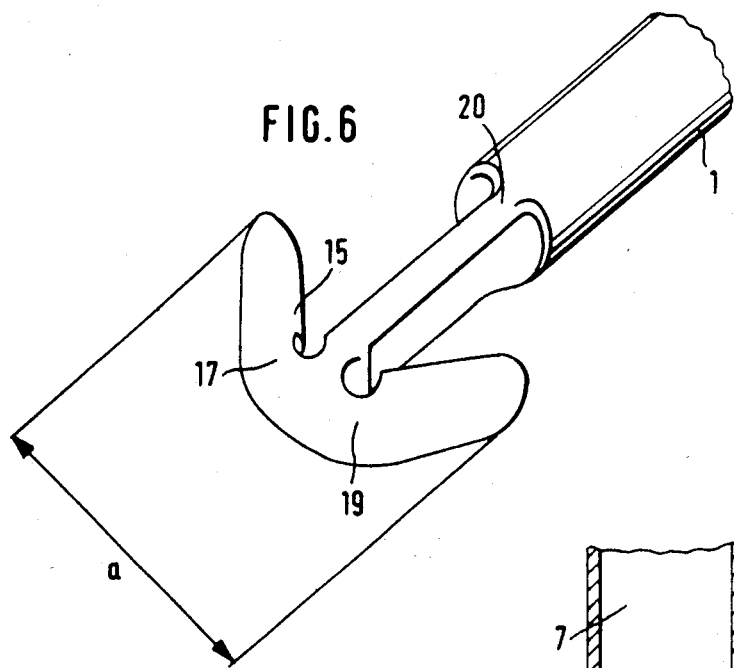

FIG. 6 a perspective view of the distal end of another embodiment.

Figure 7:
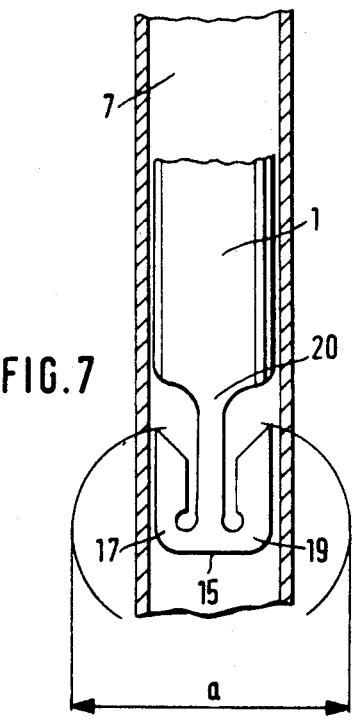

FIG. 7 a section through channel 7 with the distal end according to FIG. 6.

The central part of the device preferably has a cylindrical cross-section, is soft and is made from a plastic material, such as medical nylon and which is medically inactive. It is approximately 1 cm long and has a diameter of 1 to 2 mm. However, it is also possible to use other dimensions, in order to adapt to the function and anatomy of the isthmian channel. Its distal outer end must be soft or rounded, in order to prevent any injuries in this area. The proximal area 4 can be widened, in order to adapt to the funnel shape of the entrance of the funnel-shaped ectasia.

The distal loop is preferably made from surgical nylon or some other soft material, which is medically inactive. According to a preferred embodiment, the loop is oval and has a diameter of 3 to 6 mm, the distal end being formed by an acute angle or a rounded portion 3, in order to facilitate insertion. The two shown parts 6a, 6b can easily be moved towards one another in order to guide them in channel 7 of hysteroscope 8 and to move them into the isthmian channel 9. Subsequently, these parts can be spread apart again, when they are in their desired position, in order to prevent an undesired movement of device 1 in the direction of the uterus.

The diameter of this filamentary, distal loop 6 is preferably approximately half the diameter of central part 1.

According to a modified embodiment, the central part 1 can be provided with a plurality of small branches 10, which point to the direction of the proximal ends, in order to prevent sliding back into the uterus and curvatures to adapt to the surrounding area.

Preferably, the proximal loop 11 is constructed in a similar manner to the distal loop 2, the two parts 11a, 11b also being movable towards one another in channel 7 of hysteroscope 8. In the uterus 12, they move resiliently apart and prevent any migration of device 1 in the direction of the abdominal cavity. Loop 11 is used for the withdrawal of the device through the hysteroscope by means of forceps or a clamp arranged in insertion channel 7 in per se known manner.

According to a further embodiment of FIG. 3, small elastic branches 13a, 13b can be provided to prevent device 1 from migrating in the direction of the abdominal cavity. They also permit a reciprocal approximation in insertion channel 7 and can be spread apart in uterus 12 after reaching their operative position.

According to another embodiment, it is also possible to provide a blind channel 14, according to FIGS. 1 or 3, in the vicinity of the proximal end of device 1, in order to permit the insertion of a metal guide member 15, which is flexible and facilitates insertion and the guidance of device 1 in situ.

According to another preferred embodiment, the device can be provided with a medium which is transparent to X-rays. This can be provided either by an axial additive or through the medium being in the mass of a metallic substance. However, it can also be a chemical medium, which has a certain radiopacity.

According to another embodiment, a pharmacodynamic, physical or chemical effect can be desired, for which purpose the surface of the device is provided with chemical-medicamentous, metal coatings or invariable alloys.

As stated hereinbefore, the device is inserted by means of a hysteroscope. To this end, the tubular pessary is placed in the insertion channel 7 of the endoscope and is moved forwards by means of a metal or plastics guide wire 15 until the device has reached the end position shown in FIG. 2.

FIG. 4 shows a perspective view of the distal end of a further embodiment. In this case, the distal end is constructed as a barb 16, which is eccentric to the central portion 1 i.e. the barb 16 forms an eccentric extension of central portion 1 towards the distal end, before the barb bends towards the proximal end. As can be gathered from FIG. 5, at the point of the greatest bending of barb 16 a weak point 17 is provided, whose cross-section is consequently smaller than the barb 16 in general. This makes it possible to influence the elasticity or spring rigidity of barb 16. FIG. 4 shows the inoperative position outside channel 7, in which the outer end of the sharp barb 16 is spread outwards elastically by amount a. The diameter of central portion 1 is in this case 1 mm, so that the diameter of barb 16 is correspondingly smaller.

FIG. 5 shows the distal end within channel 7 of the hysteroscope. Barb 16 located at the distal end has in this case a total length of 3 mm. The outer end of barb 16 is in this case resiliently bent to such an extent that the distal barb 16 is approximately U-shaped and, with the exception of the aforementioned eccentric connection 18, is not in contact with central portion 1. This has the advantage that barb 16 can be readily housed in channel 7, which in this case has an internal diameter of 1.2 mm. Once again the maximum spread dimension a is obtained, which is in this case eccentric with respect to central portion 1.

FIGS. 6 and 7 show another embodiment with a double hook 15, so that the latter has two weak points 17 and 19. The connection 20 of hook 15 to central portion 1 is in this case central. Generally hook 15 and central portion 1 are constructed in one piece. The spread amount a is in this case the same on either side, as can be gathered from FIG. 6.

FIG. 7 shows the same distal end according to FIG. 6, when fitted into channel 7. The dimensions are the same as in the preceding embodiment.

Numerous variants are possible to the embodiments described hereinbefore without passing beyond the scope of the invention.

I claim:

1. A pessary for reversible contraception by obturating the isthmian channel, comprising: a body with a central part elongated along an axis and made from medically inert material, said central part having a cross-section normal to said axis with dimensions such that it forms a fluid-sealing fit with the wall of a fallopian tube in which it is inserted, said central part having a distal end and a proximal end; engagement means at said proximal end to be grasped to withdraw the pessary from the tube; and retention means extending from said distal end of said body, said retention means comprising an axially-extending support leg, and a barb arm, said support leg and barb arm forming a continuous structure with a springily flexible portion, said barb arm having a tip end which, in the relaxed unflexed condition of the flexible portion projects to a radial distance beyond the radius of the central part, whereby the tip end makes contact with said wall to resist removal of said pessary by peristaltic action, said barb arm being laterally retractable against the springy response of said flexible portion such that the tip end moves within said radius so the body and retention means can be fitted into a hysteroscope for insertion into the tube.

2. A pessary according to claim 1 in which the flexible portion constitutes a region of reduced cross-section, whereby to be more flexible than either the support leg or the barb arm to provide for said retractability of said barb arm.

3. A pessary according to claim 1 in which the support leg is centrally mounted at the distal end, and there is a plurality of said barb arms carried by it, said barb arms being angularly spaced apart.

4. A pessary according to claim 1 in which the support leg is mounted near the side of the distal end, and further includes a laterally-extending portion to which the barb arm is attached.

5. A pessary according to claim 1 in which the tip end of the barb arm is tapered to provide a reduced thickness at said to tip end.

6. A pessary according to claim 5 in which the side of the barb arm which is external when the barb arm is retracted is generally straight, the taper being formed by relieving the other side, from the tip.

* * * * *